United States Patent [19]

DeLuca-McElroy

[11] 4,234,681

[45] Nov. 18, 1980

[54] IMMOBOLIZED LIGHT EMITTING SYSTEMS

[75] Inventor: Marlene A. DeLuca-McElroy, La Jolla, Calif.

[73] Assignee: The Regents of the University of California, Berkeley, Calif.

[21] Appl. No.: 926,642

[22] Filed: Jul. 21, 1978

Related U.S. Application Data

[63] Continuation-in-part of Ser. No. 750,436, Dec. 14, 1976, abandoned.

[51] Int. Cl.$^3$ ................. C12Q 1/66; C12N 11/18; C12N 11/14; C12N 11/10
[52] U.S. Cl. .................. 435/8; 23/230 B; 435/175; 435/176; 435/177; 435/178; 435/181
[58] Field of Search ............ 195/63, 68, DIG. 11, 195/103.5 R, 103.5 L, 99; 23/230 B; 435/8, 176, 175, 177, 178, 181

[56] References Cited

U.S. PATENT DOCUMENTS

| | | | |
|---|---|---|---|
| 3,817,837 | 6/1974 | Rubenstein et al. | 195/103.5 R |
| 3,940,250 | 2/1976 | Plakas et al. | 23/230 B |

OTHER PUBLICATIONS

Erlanger, et al., Insoluble Bacterial Luciferases: A New Approach to Some Problems in Bioluminescence, Biochemical and Biophysical Research Comm. vol. 40, No. 1 1970 (pp. 70-76).
Picciolo, et al., Applications of Luminescent Systems to Intectidus Diseased Methodology, Goddard Space Flight Center, Greenbelt, Maryland, 1976 (pp. 1-4).
Waters, et al., Flavin binding by Bacterial Luciferase: Affinity Chromatography of Bacterial Luciferase, Biochem. Biophys. Res. Comm., vol. 57, No. 4, 1974 (pp. 1152-1158).
Hommerstedt, R. H. An Automated Method for ATP Analysis Utilizing the Luciferi-Luciferase Reaction Analytical Biochemistry, vol. 52, 1973 (pp. 449-455).
Brolin, et al., Photokinetic Micro Assay Based on Dehydrogenase Reactions and Bacterial Luciferase, Analytical Biochemistry. vol. 42, 1971 (pp. 124-135).
Stanley P. E., Determination of Subpicomole Levels of NADH and FMN Using Luciferase and the Liquid Scintillation Spectrometer, Analytical Biochemistry, vol. 39, 1971 (pp. 441-453).
Weetall, H. H., Immobilized Enzymes, Antigens, Antibodies and Peptides, Marcel Dekker, Inc. N.Y., 1975 (pp. 17, 18 & 74-80).
Weetall H., Applications of Immobilized Enzymes, Analytical Chemistry, vol. 48 No. 7, 6, 1976 (pp. 544A-548A, 550A, 554A, 556A, 557A & 558A).

*Primary Examiner*—David M. Naff
*Attorney, Agent, or Firm*—Phillips, Moore, Weissenberger, Lempio & Majestic

[57] ABSTRACT

Light emitting systems are immobilized on a support to provide a localized, concentrated release of light that increases the sensitivity of detection systems when assaying bio-materials. A preferred immobilized light emitting system contains an oxidoreductase and luciferase bound to glass beads that are attached to an elongated glass rod.

7 Claims, No Drawings

IMMOBOLIZED LIGHT EMITTING SYSTEMS

CROSS-REFERENCE TO RELATED APPLICATION

This application is a continuation-in-part of copending application Ser. No. 750,436, filed Dec. 14, 1976, now abandoned.

BACKGROUND OF THE INVENTION

The present invention relates to biochemical diagnostic and assay methods and more specifically to the determine of very small quantities of chemical species involved in life processes, e.g., enzymes and enzyme substrates, antigens and antibodies, etc. This invention specifically relates to those analytical methods in which a chemical species to be determined, generally a bio-material, is coupled through intermediate reactions or reacts directly in an electromagnetic signal-generating system in which the species, or its progeny in the case of intermediate reactions, is converted into an end product with the concomitant release of electromagnetic radiation.

Life processes involve a staggering variety of biochemical reactions, all interrelated, and occurring either simultaneously, or in carefully regulated sequences. Many processes that may involve relatively massive amounts of materials, e.g. metabolic processes, may, in turn, be regulated by minute amounts of bio-materials, e.g. enzymes or hormones. In other instances, malfunctions and/or diseases of the organism may release extremely small amounts of biomaterials from their normal environments into other systems of the organism. The detection and quantification of these biomaterials, both in their normal environment and in abnormal environments can yield a great amount of information concerning the functioning of both major and minor systems in the organism, and can indicate system malfunction and/or disease, as well as invasion by foreign bodies such as bacteria or viruses. Such a bio-material is thus generally defined as any chemical compound found in living organisms.

In recent decades, various techniques have been developed for determining very small quantities of biomaterials. These techniques may utilize, for instance, radioactive tracer techniques, fluorometric techniques, colored dye development, bioluminescence, chemiluminescence, etc. Such techniques depend on inherent characteristics of the materials of interest that give rise to signals that can be detected on suitable instrumentation; or by combining or associating materials that generate, or can be induced to generate such signals, with the molecular species of interest.

The particular analytical technique to which this invention specifically relates involves electromagnetic radiation generating reactions, more particularly those electromagnetic radiation generating systems in which light is produced either by the reaction of a bio-material with a protein or by the enzyme-potentiated reaction of the material with a second chemical species. Such systmes derived from living systmes and which involve proteins, including enzymes, are defined herein as bioluminescent reactions. They have been extensively discussed in the literature. For example, see Johnson et al in *Photophysiology*, Vol. 7, pages 275-334 (1972). The sources of reagents for such reactions as well as purification techniques for the reagents are well known. By "electromagnetic radiation generating" applicant means chemical systems which emit electromagnetic radiation upon the reaction of the system components with one another, whether or not the reaction requires a catalyst, whereby at least one product is yielded which was not a component of the unreacted system.

The electromagnetic radiation produced by bioluminescent reaction systems is, directly proportional to the amount of the reaction limiting component available for entering into the reaction. By way of illustration, light is produced when the enzyme, luciferase, acts to oxidize the substrate, fire-fly luciferin, in the presence of co-factor, adenosine triphosphate (ATP) and oxygen. The reaction may be summarized:

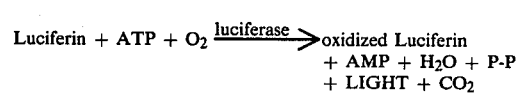

Where AMP is adenosine monophosphate, and P—P is disphosphate. The oxidation of each luciferin molecule yields a specific quantity of light, with the total light yield being directly proportional to the number of molecules oxidized. Thus, a measurement of the light yield indicates the number of luciferin, ATP, or oxygen molecules entering into the reaction, depending upon which of the three components is in molar excess, or the activity of the catalyst, luciferase.

If ATP is the least abundant species, then the reaction will cease when all the ATP is used up; or, if oxygen is the least abundnant, then when all the oxygen is used up. By the same token, the activity of the luciferase can be ascertained, if its activity is the limiting factor in the reaction process. The most accurate and complete results are obtained by ensuring a molar excess of all the components of the bioluminescent system other than the one of unknown concentration or activity to which the assay is directed.

Similar considerations apply in the use of the bacterial luciferase system for analysis of chemical species, e.g. bio-materials. Here, bacterial luciferase catalyzes the oxidation of reduced flavin mononucleotide with oxygen in the presence of a long carbon chain aldehyde to yield light, among other products. This system is typically employed to determine reduced flavin mononucleotide. The flabin mononucleotide may be the product of a reaction or series of reactions in which the flavin mononucleotide is eventually produced in a quantity that is directly proportional to a chemical species reacted at the first of the series. For example, dehydrogenases such as flavin mononucleotide oxidoreductase will oxidize the reduced from of nicotine adenine dinucleotide, which in turn may be produced by other dehydrogenases, to reduced flaving mononucleotide. The product flavin mononucleotide is then employed as the limiting component in the bacterial luciferase system. The light so generated is a measure of the original reduced nicotine adenine dinucleotide. A multiplicity of reactions of this nature may be coupled together to yield a product which is determinable by a bioluminescent reaction. As a consequence, any chemical species which can be reated to eventually yield a stiochiometrically equivalent quantity of ATP or reduced flavin mononucleotide may be assayed, respectively, by the fire-fly and bacterial luciferase systems. The prior art has employed the foregoing bioluminescent reactions in qualitative or quantitative coupled and direct assays. For example, see Hammerstedt, "Analytical Biochemistry" 52:449–455 (1973); Brolin et al., "Analytical Biochemistry" 39:441–453 (1971); and Mansberg, U.S. Pat. No. 3,679,312. In those cases where these assays have heretofore been conducted in a liquid environment all of the reagents were in solution and thus distributed homogeneously throughout.

When assaying for very low quantities of chemical species, or very low activities of enzymes, the quantity of electromagnetic radiation generated by processes such as noted above, is correspondingly small. In addition, since the reactions have heretofore been carried out in solution, the radiation emitting components are dilute and the radiation is emitted throughout a volume whereby the radiation intensity is lower than if high concentrations of reagents could be employed. This adversely affects the assay sensitivity. In addition, the larger and more opaque the volume of liquids, the greater is the possibility of self-absorption of the emitted radiation before it can leave the solution and be detected by suitable instrumentation. Finally, prior techniques measure the radiation as light emitted from a transparent container. However, irregularities in the container wall will scatter the light unpredictably, thus introducing variation into the assay.

Another detriment of conducting electromagnetic radiation assays in solution is the loss of costly reactants such as, for instance, enzymes and co-enzymes. Generally, there is no simple means of recovering such materials from solution, and they must, therefore, be discarded and replaced by new reactants for each successive assay.

In order to conserve costly enzyme materials and recover them for subsequent use, it has become well known in the art to immobilize various enzymes to insoluble support members or to one another so that the material is not lost or leached into solution during the reaction processes. See, for instance, U.S. Pat. Nos. 3,925,157 to Hamsher; 3,930,950 to Royer; 3,959,079 to Mareschi et al; 3,542,662 to Hicks et al, all of which describe various means and materials for attaching enzymes to support materials. H. H. Weetall has reviewed the chemistry of enzyme immobilization in "Analytical Chemistry" Volume 46, pages 602A et. seq., (1974) and the applications of immobilized enzymes has been discussed in "Analytical Chemistry," Volume 48, pages 544A et. seq. (1976). The prior art has, however, not disclosed immobilizing bioluminescent proteins such as the luciferases so that they can be recovered from the test solution and used over. Similarly, it is heretofore unknown to immobilize flavin mononucleotide oxidoreductase.

OBJECTS OF THE INVENTION

It is an object of the invention to immobilize onto a solid support at least one component of an electromagnetic radiation generating bioluminescent system.

It is another object of the invention to provide a method for concentrating and intensifying the electromagnetic radiation emitted during the course of chemiluminescence.

It is still another object of the invention to immobilize and concentrate bioluminescent systems that emit visible light during reaction with suitable substrates in a liquid environment.

It is yet another object of the invention to provide methods for assaying very small quantities of chemical species by coupling said species, or reaction products from said species, with bioluminescent reactions, wherein at least one bioluminescence generating component is concentrated and immobilized on a solid support.

It is still another object of the invention to covalently bond bacterial luciferase and flavin mononucleotide oxidoreductase enzymes while retaining sufficient enzyme activity to employ the enzymes in assays.

It is an additional object of the invention to provide an article for introducing at least one component of a chemiluminescent system into a liquid environment without loss of said component into the environment.

It is a further object of the invention to eliminate the variation in chemiluminescent an bioluminescent assays performed in a liquid environment which is opaque or variably opaque to the electromagnetic radiation generated by said chemiluminescent and bioluminescent systems or wherein the walls of the liquid container are irregular.

Other objects and advantages of the invention will become apparent from the following description and claims appended hereto.

SUMMARY OF THE INVENTION

The foregoing objects are achieved in prior art analytical processes in which a chemical species is assayed by reacting said species with an electromagnetic radiation generating system distributed substantially homogeneously throughout a reaction environment, followed by detection of the generated radiation as a measure of said species. In the present invention, the prior art analytical processes are improved by immobilizing at least one component of the electromagnetic radiation generating system within a localized region of the reaction environment. Hence, the generated radiation is concentrated at a single point or region of emission rather than throughout the entire environment in which the reaction takes place.

DETAILED DESCRIPTION OF THE INVENTION

The electromagnetic radiation generating component is generally immobilized on a support which is insoluble in the reaction environment, oridinarily liquid solutions, and particularly aqueous solutions. However, the component may be treated to render it insoluble without the use of a support, for example, by polymerizing the component. It is preferred to bond the component to the support in such a fashion that the component will only leach into solution in insignificant quantity. This is highly important in ensuring the reliability of the assays when using an immobilized component over a multiplicity of tests since otherwise the net activity of the component in the test will decrease steadily over use, and the results so obtained will change unless standards are prepared with impractical frequency. Of course, this loss in activity would also lower the sensitivity of the assay. Hence, it is preferred to covalently bond the component to the support.

In the case of the bacterial luciferase system, for example, FMN can be insolubilized upon a support according to the method of Waters et al; "Biochem. Biophys. Research Comm." 57 (4):1152–1158 (1974). I have found that such insoluble FMN can be reduced by FMN oxidoreductase acting upon reduced pyridine nucleotide. The insolubilized, reduced FMN will in turn participate in the ordinary soluble bacterial luciferase system. However, just as in the case of insolubilized luciferase, light is released only at the site of the insolubilized reduced FMN. In sum, the localized, concentrated release of light which forms the basis of this invention is best obtained by covalently bonding one or more of the electromagnetic radiation generating system components to an insoluble support.

The means of attachment to the support may be any one of a number of known methods that have been used to immobilize enzymes and similar bio-materials. It is only necessary that the attachment procedure does not impair the functionality of the immobilized component. It is also advantageous to have as much as possible of the component concentrated on the surface of the support material so that, (1) it will be readily accessible to the other reaction components, and (2) the emitted radiation will not be masked or absorbed by the support material. Radiation transparent support materials, such as glass, are particularly suitable and are preferred for use in the invention procedures.

The support material is most conveniently in the form of rods, strips or similar shapes that may be immersed into reaction solutions, and easily handled, cleaned, and stored for subsequent use and re-use.

It is most usual in the case of bioluminescent systems to immobilize enzymes, since they are susceptible to multiple reuse and are, most generally, the costliest component of the bioluminescent systems. Enzymes may be immobilized and insolubilized by suitable well-known techniques. An extensive review of such techniques as well as support materials is set forth in "Methods in Enzymology", Academic Press, 1974.

The support may be selected from a large number of materials. The basic properties of the support are, (1) an ability to immobilize or "fix" a component of the electromagnetic radiation generating system by either physical or chemical bonding means without (2) interfering with the activity of the "fixed" component. The support should also (3) be capable of immobilizing or concentrating a relatively large amount of the component over as limited a surface of volume as possible. Thus, it should have a high surface concentration of binding sites. Also, it is desirable to use porous or convoluted surfaces.

A great number of materials are suitable, among which are synthetic organic polymers such as acrylics, polyacrylamides, polyacrylic acids, methacrylates, styrenes, nylons, etc.; carbohydrate polymers such as Sephadex, agarose such as sepharose, and derivatives; all types of cellulosics, including cellulose products and their derivatives; and miscellaneous materials such as silicas, insoluble proteins, clays, resins, starches and the like. However, the preferred materials are those materials that are optically transparent and interfere to a minimum extent with the transmission of the electromagnetic radiation generated from the immobilized components "fixed" upon their surface.

Among the carbohydrate polymers, a derivative form of agarose with active groups, or "covalent linkage arms", of N-hydroxy sucinimide ester has been found particularly suitable. Such agarose is available under the names of "CH-Sepharose 4B" from Pharmacia Chemicals and "Affi-Gel" from Bio-Rad Laboratories.

Porous glasses, especially those of the arylamine or alkylamine types available from Corning glass, Biological Products Div., are highly suitable for use as support material. Such porous glasses react with the enzymes that comprise bioluminescent systems to provide strong, nonleaching covalent bonds; they are inert and stable over extended periods of use; and they are transparent to the emitted radiation.

The porous glasses are available in the form of find loose beads. For the purposes of the invention, it is desirable to immobilize the component onto rods or sticks in order to concentrate and localize the emitted radiation to the greatest extent possible. The immobilization of the component in rod form also facilitates insertion of the immobilized component into standard cuvets.

Chemical species not directly involved in the radiation producing reacion may also be assayed through reaction coupling techniques as described above wherein the product of one reaction is utilized as a reactant in a subsequent reaction. A final reaction product is utilized as an essential and limiting reactant in the radiation producing reaction to determine the control the amount and intensity of radiation emitted from the final reaction. The concentration or activity of the original species can then be calculated from the radiation emitted in the final reaction.

If the immobilized radiation generating component is subject to chemical reversibility to its form prior to radiation generation or if it undergoes no net change in structure during the radiation emitting reaction as is, respectively, the usual case with coenzymes and enzymes, repeated use is possible. Thus, the costly component is conserved and repetitive assays expedited.

The concentration and localization techniques can be applied to various types of electromagnetic radiation generating systems. Bioluminescent systems such as the fire-fly luciferin-luciferase-ATP reaction or the bacterial luciferase reaction involving flavin coenzymes are particularly adaptable to the present techniques. The bacterial luciferase system is additionally valuable in that they are readily coupled to oxidoreductase reactions, especially those utilizing nicotinamide adenine dinucleotide (NAD+), and/or nicotinamide adenine dinucleotide phosphate (NADP+), which are involved in a great number of bio-systems. The fire-fly luciferin-luciferase reaction is also especially valuable since it is readily coupled to the ATP coenzyme producing systems that are broadly involved in bio-energy transfer systems.

Similarly, chemiluminescent systems may be readily employed in the method of this invention. For example, luminol can be entrapped within or covalently bound to an insoluble matrix and then used in a conventional assay for oxidizing agents such as hydrogen peroxide. Again, the emitted light is generated in the same reaction that is used to detect and indicate the chemical species being tested for, and the light is generated in a highly concentrated form at a localized point with the reaction environment.

The basic principles of the invention may be better understood by considering the following specific detection system:

A number of bacterial species, e.g., Photobacterium fisheri, Photobacterium phosphoreum, and Beneckea harveyi, are known to generate visible light. It has been determined that this light generation involves the specific reaction of the bacterial enzyme, luciferase, with a co-factor, flavin monoucleotide (commonly abbreviated, FMN) to produce light.

More specifically, the light producing reaction occurs when luciferase catalyses the oxidation of the reduced form of co-factor, flavin mononucleotide, $FMNH_2$, to the oxidized form, FMN, in the presence of a long chain aldehyde substrate and oxygen. The reaction may be written:

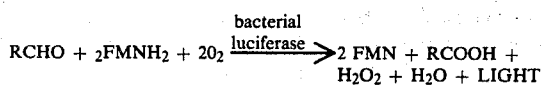
$$RCHO + 2FMNH_2 + 2O_2 \xrightarrow{\text{bacterial luciferase}} 2\ FMN + RCOOH + H_2O_2 + H_2O + LIGHT$$

Where RCHO may be any long chain aldehyde having from about 8–14 carbon atoms. Decanal, tridecanal, dodecanal, undecanal, etc. are suitable aldehydes for the substrate.

The light emitted in the reaction is directly proportional to the number of molecules undergoing reaction. Measurement of the emitted light, therefore, indicates the least abundant molecular species present as the substrate or cofactor; or should the luciferase be the reaction limiting factor, then the light emitted is an indication of the enzyme's activity.

The bacterial luciferase is immobilized on arylamine porous glass beads. The beads have been previously glued on a thin glass rod. Any suitable glue material is used to tightly adhere the beads to the rod. A standard epoxy glue is useful for this purpose. The luciferase is coupled to the porous glass beads utilizing a diazotization procedure like that disclosed in the publication "Methods in Enzymology", the Academic Press, New York, pages 59–72.

Briefly, the high silica porous glasses contain nitoraryl groups formed by the amide coupling of nitrobenzoyl chloride thereto. The nitroaryl are then reduced to amino-aryl groups by either sodium dithionite or LiAlH$_2$. The aminio-aryl group are activated by diazotization to provide coupling sites for the luciferase. The luciferase in a buffered aqueous solution (pH7) is then placed into contact with the beaded rods for 16 hours to effect coupling of the enzyme to the porous glass. The excess, uncoupled enzyme is then washed from the rods and the rods are stored in buffer solution at reduced temperature for subsequent use. If carefully handled, and thoroughly rinsed after each use, the rods with the immobilized luciferase may be reused an indefinite number of times without significantly affecting the enzyme activity.

It has recently been surprisingly discovered that dithiothreitol, a component for maintaining enzyme activity during enzyme purification and storage, should preferably be removed during immobilization of the enzymes. Failure to remove dithiothreital during enzyme immobilization greatly reduces the enzume activity recovered after immobilization. Thus, enzymes to be immobilized, such as luciferase, may be dialyzed against, for example, 0.1 M potassium phosphate at pH 7, for about 16 hours to remove the dithiothreitol prior to immobilization.

Additionally, it has been found that an initial incubation storage of the immobilized enzymes, such as upon rods, in a buffer solution for about 24 hours at a reduced temperature of about 4° C., is preferably followed by storage at about −20° C. Upon storage at about −20° C. there is a slow but significant increase in immobilized enzyme activity with time which peaks at about 7 to 10 days. The immobilized enzymes are then very stable during storage at about −20° C., may be used a number of times, and refrozen several times. The immobilized enzymes are stable at room temperature during use. Thawing and refreezing of the support for the immobilized enzymes, when such support is a glass rod, may weaken the glass supports and the rods may be subject to shattering. The addition of about 15% glycerol increases the stability of the glass rods during storage, but without any effect on enzymatic activity.

The same immobilization technique may be employed for other bioluminescent enzymes, and proteins.

In order to conduct an assay, the rod with immobilized luciferase is dipped into a solution containing all the other components or reactants necessary to produce the radiation generating reaction except for the species being assayed. The species is provided, if at all, by the test sample. Since at least one of the essential components is immobilized on the support, the radiation generating reaction takes place directly on the support surface. It is, therefore, only necessary to enclose the reaction mixture and immersed rod within the confines of a photometer sample chamber while the radiation generating reaction takes place. All of the soluble components can be combined, the sample chamber closed and the rod immersed, whereupon a flash occurs. Alternatively, it is preferred to immerse the rod in solution which is complete but for one or more reagents, or sample, followed by closing the sample chamber. Addition of the missing reagent or the sample will then produce a flash. Suitable electronic circuitry may then be utilized to measure the peak or total radiation emitted from the reaction. The radiation intensity or total radiation emitted measures the quantity of the least abundant molecular species necessary for the radiation emitting reaction; or alternately, the activity in the case of enzymes or other catalytic materials.

The radiation which is emitted by the test system of this invention may be determined by the Aminco Chem-Glo ® Photometer. This highly accurate and sensitive instrument is conveniently employed with the method and article of this invention. The instrument is equipped with a reaction chamber that holds cuvets for the reaction, as well as ports for the injection of various components while the sample is contained in the instrument.

Suitable apparatus is also commercially available for recording the radiation output detected by the photometer.

Turning to the fire-fly luciferase reaction discussed above, fire-fly luciferase requires ATP for the light emitting reaction. ATP, in turn, is a universal energy source is a vast number of a bio-reactions, and its presence, or absence, in such systems is a unique measure of many bio-reaction reactants and products.

Typical ATP producing systems are, by way of illustration; sugar synthesis systems wherein phosphenol pyruvate in the presence of co-factor adenosoine diphosphate and the enzyme pyruvate kinase yields pyruvate and adenosine triphosphate (ATP). Other systems are muscle contraction systems, wherein creatine phosphate is converted into creatine while its co-factor adenosine diphosphate converts to ATP in the presence of the enzyme, creatine phosphokinase ATP assays can also, for instance, be useful in determining bacterial content in urine, waste products, wine, beer, milk, and, in general, biomass measurements. Hence, the measurements of ATP in any bio-system can be utilized as a measure of ATP co-factors, substrates, and related enzymes.

It has been noted before that ATP is a co-enzyme in the light producing luciferin-luciferase reaction. As a consequence, the light generated from a luciferin-luciferase reaction will assay ATP quantitatively wherein the ATP is the limiting component in the reaction and qualitatively, otherwise. An assay of ATP, in turn may be used to calculate the abundance of chemical species which yield or metabolize ATP.

In a similar manner, the bacterial luciferase reaction may be coupled back to a vast number of bioreactions. Consider the following coupled reactions:

$$\text{Bio-material to be assayed} + \text{NAD (or NADP)} \quad (1)$$
$$\xrightarrow{\text{Enzyme}} \text{NADH (or NADPH)} + \text{Product}$$

$$\text{NADH (or NADPH)} + \text{FMN} \quad (2)$$
$$\xrightarrow{\text{NAD: FMN OXIDOREDUCTASE}} \text{FMNH}_2 + \text{NAD (or NADP)}$$

$$\text{RCHO} + \text{FMNH}_2 + \text{O}_2 \quad (3)$$
$$\xrightarrow{\text{Immobilized Bacterial Luciferase}} \text{FMN} + \text{RCOOH} + \text{H}_2\text{O} + \text{H}_2\text{O}_2 + \text{LIGHT}$$

Where NAD refers to nicotinamide adenine dinucleotide, NADP refers to nicotinamide adenine dinucleotide phosphate, and NADH and NADPH ar the reduced forms, respectively. FMN, FMHN$_2$, RCHO, and RCOOH have been defined hereinbefore.

Reaction (3) has been set forth before and defines the bacterial luciferase light producing reaction that is measured according to the principal method of the invention. Reaction (2) is an oxidation-reduction reaction which is catalyzed by the NAD:FMN oxidoreductase that is obtained by known methods from bioluminescent bacteria such as Beneckea harveyi. For example, the oxidoreductase is separated from the bacterial luciferase during the purification thereof by well-known chromatographic techniques. Thus, when luciferase is purified by chromotography on DEAE-Sephadex, the reductase elutes before the luciferase and may be collected as a separate fraction. Reaction (1) is any of a large number of bio-reactions in which NAD (or NADP) are necessary co-factors. A few examples of such NAD or NADP requiring reactions are:

$$\text{Alcohol} + \text{NAD (or NADP)} \xrightarrow{\text{alcohol dehydrogenase}} \text{adehydes} + \text{NADH (or NADPH)}$$

$$\text{2,3-Butanediol} + \text{NAD} \xrightarrow{\text{butanediol dehydrogenase}} \text{acetoin} + \text{NADH}$$

$$\text{glycerol} + \text{NAD} \xrightarrow{\text{glycerol dehydrogenase}} \text{dihydroxyacetone} + \text{NADH}$$

$$\text{xylitol} + \text{NAD (or NADP)} \xrightarrow{\text{D-xylulose reductase (L-xylulose reductase)}} \text{D-xylulose (L-xylulose)} + \text{NADH}$$

$$\text{galactitol} + \text{NAD} \xrightarrow{\text{galactitol dehydrogenase}} \text{D-tagatose} + \text{NADH}$$

$$\text{L-gluconate} + \text{NADP} \xrightarrow{\text{glucuronate dehydrogenase}} \text{D-glucuronate} + \text{NADPH}$$

$$\text{alditol} + \text{NADP} \xrightarrow{\text{aldose reductase}} \text{aldose} + \text{NADPH}$$

$$\text{glycollate} + \text{NAD} \xrightarrow{\text{glyoxylate reductase}} \text{glyoxylate} + \text{NADH}$$

$$\text{L-lactate} + \text{NAD} \xrightarrow{\text{lactate dehydrogenase}} \text{pyruvate} + \text{NADH}$$

$$\text{L-malate} + \text{NAD} \xrightarrow{\text{malate dehydrogenase}} \text{oxalaacetate} + \text{NADH}$$

-continued $$\beta\text{-D-glucose} + \text{NAD (or NADP)} \xrightarrow{\text{glucose dehydrogenase}} \text{D-glucone-}\delta\text{-lactone} + \text{NADH (or NADPH)}$$

$$\text{androsterone} + \text{NAD (or NADP)} \xrightarrow{\text{3-}\alpha\text{-hydroxy steroid dehydrogenase}} \text{androstane-3, 17-dione} + \text{NADH (or NADPH)}$$

$$\text{20-dihydrocortisone} + \text{NAD} \xrightarrow{\text{cortisone reductase}} \text{cortisone} + \text{NADH}$$

$$\text{pyridoxin} + \text{NADP} \xrightarrow{\text{pyridoxin dehydrogenase}} \text{pyridoxal} + \text{NADPH}$$

$$\text{mannitol} + \text{NAD} \xrightarrow{\text{mannitol dehydrogenase}} \text{fructose} + \text{NADH}$$

$$\text{aldehyde} + \text{NAD} + \text{H}_2\text{O} \xrightarrow{\text{adehyde dehydrogenase}} \text{acid} + \text{NADH}$$

Many other similar NAD or NADP co-factor reactions are known and the above are merely illustrative.

In any event, it is clear that a great number of bioreactions produce NAD or NADP in the reduced state. If such reactions (1) are coupled into the NAD:FMN oxidoreductase or NADP:FMN oxidoreductase reaction (2), it is apparent the FMNH$_2$ will be produced in accordance with the quantity of NADH (or NADPH) available from reaction (1).

If the FMNH$_2$ produced by reaction (2) is thereupon introduced into reaction (3), the bacterial luciferase reaction, the light produced thereby wil be proportional to the original quantity of pyridine nucleotide; and hence, to the dehydrogenase enzyme or its substrate which is to be determined.

Coupling the radiation producing reaction into precursor reactions as noted above leads to a variation of the immobilization procedures of the invention. Specifically, it is often advantageous to concentrate and immobilize two or more essential components for a series of reactions on a single support member. Such technique permits the direct coupling of reactions of the types (2) and (3) noted above.

In such a technique, the desired FMN oxidoreductase is immobilized on the same support as the luciferase. This yields the additional advantage of this invention that the highly oxidation labile FMNH$_2$ yielded by the NADH-FMN reaction is produced in extremely close proximity to the luciferase and thus, it is directly and immediately available to enter into the luciferase reaction. Manipulative steps are thereby reduced and losses or spurious re-oxidation of the FMNH$_2$ by the sample components or contaminants are avoided. In such specialized uses, dehydrogenases, for example, can also be bound to the support.

The following example will illustrate a double immobilization of two enzymes on a single support.

EXAMPLE

10–15 mgs. fine beads of activated arylamine glass were glued to 1.7 mm. diameter glass rods 4 cm. long. The glass rods were first dipped into Duro E-Pox.E 5 glue and then rolled into the porous glass beads. The rods and adherent beads were allowed to dry overnight. The luciferase and reductase enzymes (isolated from Beneckea harveyi) were mixed in the ratio of 1 mg. luciferase to 2.5 mgs. reductase of which 0.5 ml. aqueous solution was contacted with the rods and activated beads for 16 hours. The solution was buffered at pH 7.0 with 0.1M phosphate. The rods were then washed with 25 mls. cold 1M sodium chloride followed by 100 mls. cold distilled water to remove any unbound enzymes. The rods were then incubated overnight in 1% bovine serum albumin (BSA) in the phosphate buffer containing $5 \times 10^{-4}$M dithiothreitol (DTT). The rods were then stored in phosphate buffer containing the same amount of DTT at 4° C.

The bound enzymes were assayed, and Table I below give typical results for the binding of the enzymes to the porous glass beads and their apparent activities.

TABLE I

BINDING OF LUCIFERASE AND FMN: REDUCTASE TO GLASS RODS

|  | Luciferase Relative Light Units/ml | FMN Reduction unmoles NADH Oxid. per ml per min | Coupled assay Relative Light units/ml | mgs. Protein ml |
|---|---|---|---|---|
| (A) Original Mixture | $7.0 \times 10^6$ | .293 | $4.2 \times 10^5$ | 2.56 |
| (B) Supernatant | $2 \times 10^6$ | .100 | $2 \times 10^4$ | 1.25 |
| (C) Rods | $2.5 \times 10^3$ | .020 | $1.2 \times 10^4$ | 1.31 |
| % of Rods Apparent Activity | 0.05% | 10.3 | 3.0 | 51 |

(A) Enzymatic activities of a mixture of soluble luciferasereductase prior to coupling to the beads, original mixture. (B) After the coupling procedure the mixture was again assayed, supernatant. (C) The amount of activity associated with the rods was also assayed. The percent of activity as assayed on the rods was based on the initial total activity in the original mixture. Luciferase was assayed by injection of $FMNH_2$. FMN:Reductase was assayed by disappearance of absorbance at 340 nm and the coupled assay is the light obtained upon injection of NADH. However, as previously hereindescribed, the amount of activity associated with the rods (c) may be increased by removal of dithiothreitol during immobilization, and by storage at about $-20°$ C. for 7 to 10 days.

The enzymes, both those in solution and those immobilized on the porous glass were assayed as follows: All soluble enzyme assays were preformed at 23° C. Luciferase was assayed by injection 0.1cc $FMNH_2$, catalytically reduced with $H_2$ over platinized asbestos, into a solution containing luciferase, decanal and 0.1% BSA in 0.1M phosphate buffer pH 7.0. Final concentration of the reactants were: $2.3 \times 10^{-5}$ M $FMNH_2$ and 0.0005% decanol and 0.08 ug luciferase per ml. Light intensity was measured in an Amino Chem-Glo ® Photometer and recorded on an Aminco Recorder. The peak intensity was linear with respect to added luciferase in the range of 0.08 ug to 8 ug per ml using this instrument. Immobilized luciferase was assayed using the same concentrations of substrates. The rod containing the glass beads was placed in a test tube in the photometer and $FMNH_2$ was injected.

Soluble FMN:reductase was assayed by measuring the rate of disappearance of absorption at 340 nm in a Cary Model 14 recording spectrophotometer. The reaction was initiated by adding NADH to 1 ml of 0.015 M phosphate buffer pH 7.0—containing $7 \times 10^{-5}$ M ethylenediamine tetraacetic acid, 0.4 mgs reductase and FMN. Final concentrations were $2 \times 10^{-4}$M NADH, $1.3 \times 10^{-4}$M FMN. When the immobilized enzyme was assayed the rod containing the enzyme was dipped into the cuvet which was mixed for 1 minute intervals, then removed and the OD 340 measured. This assay was linear for at least 3 minutes.

The coupled assay was measured by peak light intensity obtained following injection of NAD(P)H into 0.5 ml of 0.1M phosphate buffer pH 7.0 containing 7.5 ug reductase, 5 ug luciferase, and $2.3 \times 10^{-6}$M FMN and 0.0005% decanal. When the immobilized enzyme was being assayed, the rod was immersed in the solution containing FMN and aldehyde. NAD(P)H was injected into the solution.

The immobilized enzymes exhibited linearity in peak light intensity as a function of either NADH or NADPH concentration. Linearity with NADH was obtained in the range of $1 \times 10^{-12}$ moles to $5 \times 10^{-8}$ moles, and for NADPH in the range of $1 \times 10^{11}$ moles to $2 \times 10^{-7}$ moles. The bound enzymes were stable and reusable.

As an additional embodiment of the invention, it is known to detect bacteria in fluid samples through the reaction of iron porphyrins, such as, peroxidase, cytochrome, catalase in microbial cells, with luminol (5-amino-2, 3-dihydro-1, 4-phthalazine-dione) to produce visible light. See, for instance, Picciolo, et al, Goddard Space Flight Center publication X-726-76-212, dated Sept. 1976, entitled "Applications of Luminescent Systems To Infectious Disease Methodology", pages 69 et. seq.

In such systems chemiluminescene is produced by the reaction of luminol with hydrogen peroxide in aqueous alkaline solution in the presence of an oxidizing activating agent such as ferricyanide, hypochlorite, or a chelated transition metal such as iron or copper. In the bacterial detection system, the iron porphyrins are considered as activators for luminol chemiluminescence.

Such a chemiluminescent system is adaptable to the method of the invention by concentrating, localizing and immobilizing the luminol on suitable support materials. The luminol may be absorbed on a support material such as those previously referred to herein.

The localized immobilized luminol, will generate a concentrated light emission upon the activator-catalyzed reaction with hydrogen peroxide. This emission may be conventionally detected using the aforementioned photometer as a measure of activator, hence bacterial, presence.

Although the description, supra, discloses and describes a number of specific examples of the methods and techniques of the present invention, it will be understood that the invention is not be limited thereby. All extension or variations of the invention as will be apparent to those skilled in the art are considered to be encompassed by the invention disclosed herein and in accordance with the claims appended hereto.

What is claimed is:

1. A product useful for comprising: a non-reactive elongated rod having an insoluble enzyme retaining material attached thereto, said enzyme retaining material being porous glass beads; an oxidoreductase enzyme immobilized on said enzyme retaining material; and luciferase enzyme also immobilized on said enzyme retaining material.

2. The product of claim 1 wherein said oxidoreductase enzyme is FMN oxidoreductase, and both said enzyme retaining material and said elongated rod are substantially transparent to light detectable by a photometer.

3. A product useful for assaying bio-materials comprising: a non-reactive elongated rod having an insoluble enzyme retaining material attached thereto, said enzyme retaining material being an agarose with N-hydroxy succinimide ester arms thereupon, and said elongated rod being glass; an oxidoreductase enzyme immobilized on said enzyme retaining material; and luciferase enzyme also immobilized on said enzyme retaining material.

4. The product of claims 1 or 3 wherein said enzyme retaining material has a high surface concentration of binding sites at which said enzymes are immobilized, and said immobilized enzymes are in intimate proximity to one another on said enzyme retaining material.

5. An assay method for chemical species that enter into enzymatic reaction with NAD or NADP as a cofactor to produce NADH or NADPH and one product thereof, comprising providing an elongate support member having porous glass beads affixed thereto, immobilizing an FMN oxidoreductase on said glass beads, also immobilizing bacterial luciferase on said glass beads, contacting said elongate support member and the immobilized FMN oxidoreductase and bacterial luciferase with an aqueous solution including the NADH or NADPH, FMN, a long chain aldehyde, and oxygen, to thereby effect a reduction of FMN to $FMNH_2$ and the oxidation of NADH or NADPH to NAD or NADP by the FMN oxidoreductase, and the subsequent reoxidation of the $FMNH_2$ to FMN by the bacterial luciferase to generate light proportional to the amount of $FMNH_2$ reoxidized, detecting and quantifying the generated light to measure the amount of $FMNH_2$ produced by the oxidation of the NADH or NADPH, and calculating therefrom the amount of chemical species necessary to produce the initial NADH or NADPH.

6. An assay method for chemical species that enter into enzymatic reaction with NAD or NADP as a cofactor to produce NADH or NADPH and one product thereof comprising:

providing a non-reactive elongated rod having an enzyme retaining material attached thereto, said rod and enzyme retaining material both being substantially transparent to light detectable by a photometer, said enzyme retaining material having immobilized thereon an FMN oxidoreductase enzyme and a luciferase enzyme;

immersing said elongated rod in an aqueous solution including said NAD or NADP, to thereby contact said immobilized enzymes with said solution;

enclosing said aqueous solution and said immersed rod within a photometric sample chamber; and, detecting a generated light flash by a photometer, said light flash generated by adding said chemical species to said aqueous solution either during said immersing step or during said enclosing step.

7. The assay method as in claim 6 further comprising:

removing said elongated rod from immersion in said aqueous solution; and, rinsing said elongated rod with a solution sufficient to prepare said elongate rod for reuse, and simultaneously retaining said immobilized enzymes on said enzyme retaining material of said elongated rod.

* * * * *

UNITED STATES PATENT AND TRADEMARK OFFICE
CERTIFICATE OF CORRECTION

PATENT NO. : 4,234,681
DATED : November 18, 1980
INVENTOR(S) : Marlene A. DeLuca-McElroy It is certified that error appears in the above—identified patent and that said Letters Patent is hereby corrected as shown below:

Title of Invention should read -- IMMOBILIZED LIGHT EMITTING SYSTEMS --.

Column 2, line 21, "disphosphate" should read -- diphosphate --.

line 31, "abundnant" should read -- abundant --.

line 46 "flabin" should read -- flavin --.

line 54 "flaving" should read -- flavin --.

Column 3, line 43, after "Chemistry" insert -- , --.

Column 4, line 43, "oridinarily" should read -- ordinarily --.

Column 5, line 40, "a surface of volume" should read -- a surface or volume --.

Column 6, line 17, "determine the control" should read -- determine and control --.

line 59, "fisheri," should read -- fischeri, --.

line 63, "monoucleotide" should read -- mononucleotide--.

Column 7, line 28, "nitor-" should read -- nitro---.

Column 8, line 20, insert -- a -- between "in" and "solution".

line 46, "source is" should read -- source in --.

line 50, "phosphenol" should read -- phosphoenol --.

UNITED STATES PATENT AND TRADEMARK OFFICE
CERTIFICATE OF CORRECTION

PATENT NO. : 4,234,681

DATED : November 18, 1980

INVENTOR(S) : Marlene A. DeLuca-McElroy

It is certified that error appears in the above—identified patent and that said Letters Patent is hereby corrected as shown below:

Column 8, line 51, "adenosoine" should read -- adenosine --.

line 57, after "phosphokinase" insert -- . --.

line 60, "measurements" should read -- measurement --.

Column 10, line 30, "wil" should read -- will --.

Column 11, line 45, "preformed" should read -- performed --.

line 51, "decanol" should read -- decanal --.

Column 12, line 22, insert -- contained -- between "catalase" and "in".

line 57, insert -- assaying bio-materials -- between "for" and "comprising".

Column 14, line 29, "elongate" should read -- elongated --.

Signed and Sealed this

Twenty-first Day of April 1981

[SEAL]

Attest:

RENE D. TEGTMEYER

Attesting Officer     Acting Commissioner of Patents and Trademarks